United States Patent
Halpern Chirch et al.

(10) Patent No.: US 11,452,685 B2
(45) Date of Patent: Sep. 27, 2022

(54) COSMETIC COMPOSITIONS PROVIDING FOR A TRANSFORMATIVE TEXTURE

(71) Applicant: L'OREAL, Paris (FR)

(72) Inventors: Susan Halpern Chirch, Basking Ridge, NJ (US); Victoria Shin-wei Fu, Monrovia, CA (US); Mariana Montoya, Berkley Heights, NJ (US); Paul Bonvallet, Westfield, NJ (US)

(73) Assignee: L'OREAL, Paris (FR)

( * ) Notice: Subject to any disclaimer, the term of this patent is extended or adjusted under 35 U.S.C. 154(b) by 183 days.

(21) Appl. No.: 15/797,657

(22) Filed: Oct. 30, 2017

(65) Prior Publication Data
US 2019/0125656 A1 May 2, 2019

(51) Int. Cl.
| | |
|---|---|
| A61K 8/92 | (2006.01) |
| A61Q 19/00 | (2006.01) |
| A61K 8/96 | (2006.01) |
| A61K 8/73 | (2006.01) |
| A61K 8/03 | (2006.01) |
| A61K 8/34 | (2006.01) |
| A61K 8/37 | (2006.01) |
| A61K 8/06 | (2006.01) |

(52) U.S. Cl.
CPC ............... *A61K 8/922* (2013.01); *A61K 8/03* (2013.01); *A61K 8/062* (2013.01); *A61K 8/345* (2013.01); *A61K 8/375* (2013.01); *A61K 8/73* (2013.01); *A61K 8/965* (2013.01); *A61Q 19/007* (2013.01); *A61K 2800/48* (2013.01); *A61K 2800/5422* (2013.01); *A61K 2800/591* (2013.01); *A61K 2800/5922* (2013.01)

(58) Field of Classification Search
CPC . A61K 8/922; A61K 8/03; A61K 8/04; A61K 8/06; A61K 8/92
See application file for complete search history.

(56) References Cited

U.S. PATENT DOCUMENTS

| | | | | |
|---|---|---|---|---|
| 2,520,980 A | * | 9/1950 | Terkel | A61Q 19/00 514/789 |
| 4,165,385 A | * | 8/1979 | Lefebvre | A61K 8/37 514/783 |
| 5,837,227 A | | 11/1998 | Zoumas et al. | |
| 6,277,364 B1 | * | 8/2001 | Bucks | A61K 8/87 424/401 |
| 7,150,876 B2 | * | 12/2006 | Chaudhuri | A61K 8/37 424/401 |
| 7,749,523 B2 | * | 7/2010 | McLaughlin | A61K 8/345 424/401 |
| 2007/0003511 A1 | | 1/2007 | Schulz et al. | |
| 2009/0130220 A1 | | 5/2009 | Johnson | |
| 2009/0285876 A1 | * | 11/2009 | Hein | A61K 8/375 424/443 |
| 2011/0144141 A1 | * | 6/2011 | Hu | A61K 8/361 514/275 |
| 2011/0305737 A1 | | 12/2011 | Alexiades-Armenakas | |
| 2012/0204894 A1 | * | 8/2012 | Odoms | A61K 8/375 132/202 |
| 2017/0216177 A1 | * | 8/2017 | Thrower | A61K 8/4953 |

FOREIGN PATENT DOCUMENTS

| | | | | |
|---|---|---|---|---|
| KR | 20040076400 A | * | 9/2004 | ............... A61K 8/04 |
| WO | 2009080005 A1 | | 7/2009 | |
| WO | 2012147042 A2 | | 1/2012 | |
| WO | 2013057118 A2 | | 4/2013 | |
| WO | 2014184228 A1 | | 11/2014 | |

OTHER PUBLICATIONS

Bataichem.cn Cosmetic care caprylyl methicone/low viscosity silicone oil improves spreadability. 3 pages. Jun. 14, 2019.*
Rimpro India. Surfactants widely used in Industrial Processes—Fatty Alcohol Ethoxylate, Fatty Acid Ethoxylate. 1 page Jun. 14, 2019.*
Dimethicone, Chemical Book << CAS DataBase List >>Dimethicone, 4 pages (Year: 2017).*
International Search Report for PCT/US2018/057999 dated Feb. 14, 2019.

* cited by examiner

*Primary Examiner* — Lakshmi S Channavajjala
(74) *Attorney, Agent, or Firm* — McNees Wallace & Nurick LLC

(57) ABSTRACT

A cosmetic composition and a method for preparing the cosmetic composition are provided. The cosmetic composition includes an aqueous phase and oil phase. The aqueous phase comprises at least one water soluble ingredient including at least one non-ionic surfactant. The oil phase comprises a transformative agent, at least one thickener and at least one solvent. The transformative agent comprising at least 1% of at least one butter and at least 1% of at least one oil, the transformative agent having a butter to oil ratio of from about 2:5 to about 9:10. The cosmetic composition has a transformative texture.

27 Claims, No Drawings

COSMETIC COMPOSITIONS PROVIDING FOR A TRANSFORMATIVE TEXTURE

FIELD OF THE INVENTION

The present invention is generally directed to a cosmetic composition having a transformative texture and a method for preparing the cosmetic composition. More particularly, the present invention is directed to a cosmetic composition having a transformative texture, the cosmetic composition comprising at least one non-ionic surfactant, a transformative agent, at least one thickener and at least one solvent.

BACKGROUND OF THE INVENTION

A variety of compositions, especially cosmetic compositions, have been developed to provide transformative skin texture. Unfortunately, many of these compositions are in fact difficult to apply and do not possess a smooth feel upon application.

Although glycerin is a fairly low cost humectant or hydrating agent, problems arise when incorporating high levels of glycerin in cosmetic compositions. Incorporating high levels of glycerin, generally greater than 5%, results in a cosmetic compositions having a tacky and sticky feel upon application to skin. The tacky or oily feel is undesirable to consumers. Several approaches, such as using light emollients, powders, or combinations thereof may reduce tackiness; however, the resulting cosmetic compositions may not provide sufficient consumer appeal and may still have residual tackiness that can be felt on the skin after application.

It is an object of the present invention to provide a cosmetic application that overcomes at least one of the aforementioned drawbacks associated with products that are hard to rub in and provide oily finish. Yet another object of the present invention is to provide a favorable environment for skin hydration or skin healing/repair and compatibility with makeup.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The compositions and methods hereof are characterized, in various embodiments, as comprising at least one non-ionic surfactant, a transformative agent comprising at least 1% of at least one butter and at least 1% of at least one oil, the transformative agent having a butter to oil ratio of from about 2:5 to about 9:10, at least one thickener and at least one solvent to impart on the skin a transformative texture upon being rubbed to provide silky/satin finish that is not present in compositions that do not have the specific transformative agent. Consumers perceive the silky/satin finish as positive skin benefits, especially desirable for a skin healing/repair product.

In an exemplary embodiment, a cosmetic composition includes an aqueous phase and oil phase. The aqueous phase comprises at least one water soluble ingredient including at least one non-ionic surfactant. The oil phase comprises a transformative agent, at least one thickener and at least one solvent. The transformative agent comprising at least 1% of at least one butter and at least 1% of at least one oil, the transformative agent having a butter to oil ratio of from about 2:5 to about 9:10. The cosmetic composition has a transformative texture.

In another exemplary embodiment, a cosmetic composition includes an aqueous phase and oil phase. The aqueous phase comprises at least one water soluble ingredient including from about 1 to about 20 wt % of at least one non-ionic surfactant. The oil phase comprises a transformative agent, from about 0.1 to about 5 wt % of at least one thickener and from about 10 to about 30 wt % of at least one solvent. The transformative agent comprising at least 1% of at least one butter and at least 1% of at least one oil, the transformative agent having a butter to oil ratio of from about 2:5 to about 9:10. The cosmetic composition has a transformative texture.

In another exemplary embodiment, a method for preparing a cosmetic application is provided. The method comprises providing an aqueous phase comprising at least one water soluble ingredient including at least one non-ionic surfactant; providing an oil phase comprising at least one butter, at least one oil, at least one thickener and at least one solvent; and mixing the aqueous phase and the oil phase.

Other features and advantages of the present invention will be apparent from the following more detailed description, taken in conjunction with the accompanying drawings which illustrate, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

"Cosmetically acceptable" means compatible with any keratinous substrate. For example, "cosmetically acceptable carrier" means a carrier that is compatible with any keratinous substrate.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

"Transformative texture", as used herein, means a texture of a composition capable of a thick initial application which thins to a smooth and/or velvet and/or satin finish upon application of mechanical shear, such as rubbing. The finish does not have an oily or greasy texture. Alternatively, "transformative texture", as used herein, means a texture that breaks slowly upon initial application and spreading upon skin, but begins to spread more easily throughout the application process which finishes and leaves a residue that is of a velvet or satin feel.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

Applicants have surprisingly discovered that cosmetic compositions including a transformative agent including from about 1 to about 10 wt % of at least one butter and from about 1 to about 10 wt % of at least one oil, the transformative agent having a butter to oil ratio of from about 2:5 to about 9:10, provide richer texture as being more efficacious for skin healing and repair than other cosmetic compositions. Without being bound by theory, it is believed that the unique ratio of butter and oil allows the cosmetic composition to leave a silky residue while creating an occlusive barrier to trap in moisture. The unique ratio of materials allows the formula to have both a thick application and a thin feeling when consumers finishes application. Furthermore, the combination of at least one butter and at least one oil provides advantageous skin properties while also leaving a silky residue that acts as gripping mechanism for foundation. The unique cosmetic compositions enable hydration of keratinous tissue, compatibility with makeup, creation of a smooth canvas for makeup, easy spreading of foundation, diminishing appearance of pores and enhancing natural skin tone.

In particular, the method according to the invention is targeted at treating or hydrating skin, improving or maintaining the hydration of skin, improving or maintaining the texture of the skin, or improving or maintaining the skin barrier function.

In some embodiments, a cosmetic composition includes an aqueous phase and oil phase. The aqueous phase comprises at least one water soluble ingredient including at least one non-ionic surfactant. The oil phase comprises a transformative agent, at least one thickener and at least one solvent. The transformative agent comprising at least 1 of at least one butter and at least 1% of at least one oil, the transformative agent having a butter to oil ratio of from about 2:5 to about 9:10. The cosmetic composition has a transformative texture.

In some embodiments, a cosmetic composition includes an aqueous phase and oil phase. The aqueous phase comprises at least one water soluble ingredient including from about 1 to about 20 wt % of at least one non-ionic surfactant. The oil phase comprises a transformative agent, from about 0.1 to about 5 wt % of at least one thickener and from about 10 to about 30 wt % of at least one solvent. The transformative agent comprising at least 1% of at least one butter and at least 1% of at least one oil, the transformative agent having a butter to oil ratio of from about 2:5 to about 9:10. The cosmetic composition has a transformative texture.

Non-Ionic Surfactant

The non-ionic surfactant in the cosmetic composition, according to the disclosure in some embodiments, is discovered to be compatible with cosmetic applications. In some embodiments, the non-ionic surfactant is one or more of stearic acid, polysorbate 20, PEG-100 stearate, sorbitan stearate, cetearyl alcohol, ceteareth-20 and glyceryl stearate.

In some embodiments, the composition includes at least one non-ionic surfactant. In some embodiments, the composition includes one, two, three or more non-ionic surfactants.

In accordance with the various embodiments, the amount of non-ionic surfactant present in the composition may be from about 1% to about 20%, alternatively from about 2% to about 19%, alternatively from about 3% to about 18%, alternatively from about 4% to about 17%, alternatively from about 5% to about 16%, alternatively from about 6% to about 15%, alternatively from about 7% to about 14%, alternatively from about 8% to about 13%, alternatively from about 9% to about 12%, alternatively from about 10% to about 11%, or any suitable combination, sub-combination, range, or sub-range thereof by weight, based on the weight of the composition. One of ordinary skill in the art, however, will appreciate that other ranges are within the scope of the invention.

Transformative Agent

In accordance with the disclosure, a transformative agent including at least one butter and at least one oil is present in the composition. In some embodiments, the transformative agent includes at least 1% of at least one butter and at least 1% of at least one oil, the transformative agent having a butter to oil ratio of from about 2:5 to about 9:10. The unique ratio of materials allows the formula to first have a thick application and then a thin feeling upon being rubbed into keratinous substrate. The thinned out formula leaves a silky residue/feeling while creating an occlusive barrier to trap in moisture.

In some embodiments, the at least one butter is one or more of butyrospermum parkii (shea) butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, macadamia nut butter and mango butter.

In some embodiments, the at least one oil is one or more of *Helianthus annuus* (sunflower) seed oil, *Sesamum indicum* (sesame) seed oil, coconut oil, jojoba oil, isopropyl palmitate, isononyl isononanoate, sesame oil, sunflower oil, apricot oil, dicaprylyl capric triglyceride, dicaprylyl carbonate and caprylic/capric triglyceride.

In accordance with the various embodiments, the amount of butter present in the composition may be at least 1%, alternatively from about 1% to about 10%; alternatively from about 2% to about 9%, alternatively from about 3% to about 8%, alternatively from about 4% to about 7%, alternatively from about 5% to about 6%, or any suitable combination, sub-combination, range, or sub-range thereof by weight, based on the weight of the composition. In accordance with various embodiments according to the disclosure, the amount of oil present in the composition may be from at least 1%, alternatively from about 1% to about 10%; alternatively from about 2% to about 9%, alternatively from about 3% to about 8%, alternatively from about 4% to about 7%, alternatively from about 5% to about 6%, or any suitable combination, sub-combination, range, or sub-range thereof by weight, based on the weight of the composition. The transformative agent may include a butter to oil ratio of from about 2:5 to about 9:10, alternatively from about 2:5 to about 4:5, alternatively from about 1:2 to about 9:10, alternatively from about 2:5 to about 7:10, alternatively from about 1:2 to about 4:5, alternatively from about 3:5 to about 9:10, alternatively from about 2:5 to about 3:5, alternatively from about 1:2 to about 7:10, alternatively from about 3:5 to about 4:5, alternatively from about 7:10 to about 9:10, or any suitable combination, sub-combination, range, or sub-range thereof. One of ordinary skill in the art, however, will appreciate that other ranges are within the scope of the invention.

In some embodiments, the at least one butter has a melting point in the range of from about 30 to about 45 degrees Celsius.

Thickener

In accordance with the disclosure, one or more thickener is present in the composition. In some embodiments, the thickener may include one or more of xanthan gum and carbomer.

In accordance with the various embodiments, the amount of thickener present in the composition may be from about 0.1% to about 5%, alternatively from about 0.5% to about 4.5%, alternatively from about 1% to about 4%, alternatively from about 1.5% to about 3.5%, alternatively from about 2% to about 3%, or any suitable combination, sub-combination, range, or sub-range thereof by weight, based on the weight of the composition. One of ordinary skill in the art, however, will appreciate that other ranges are within the scope of the invention.

Organic Solvent

In accordance with the disclosure, one or more organic solvent is present in the composition. The organic solvent present in the cosmetic composition, according to the disclosure, includes, but is not limited to, butylene glycol, C12-15 alkyl benzoate, glycerin, propylene, glycol, caprylyl glycol, or combinations thereof. Although these solvents are given as an example, it will be appreciated that other solvents compatible with cosmetic applications known in the art may be used.

In accordance with the various embodiments, organic solvent may be present in a given composition in an amount of from about 10% to about 30%, alternatively from about 12% to about 28%, alternatively from about 15% to about 25%, or any suitable combination, sub-combination, range, or sub-range thereof by weight, based on the weight of the composition. One of ordinary skill in the art, however, will appreciate that other ranges are within the scope of the invention Water In accordance with the various embodiments, water may be present in a given composition in an amount of from about 40% to about 80%, alternatively from about 45% to about 75%, alternatively from about 50% to about 70%, alternatively from about 55% to about 65% or any suitable combination, sub-combination, range, or sub-range thereof by weight, based on the weight of the composition. One of ordinary skill in the art, however, will appreciate that other ranges are within the scope of the invention.

Optional Components

In some embodiments, there may be one or more actives present in the cosmetic composition, according to the disclosure, the actives selected from, for example, humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof.

In some embodiments, there may be one or more other components present in the cosmetic composition, according to the disclosure, the other components selected from sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

In accordance with the various embodiments, the amount of actives and other components present in the composition may be from about 0% to about 50%, alternatively from about 0.5% to about 30%, alternatively from about 1.5% to about 20%, alternatively from about 5% to about 15%, or any suitable combination, sub-combination, range, or sub-range thereof by weight, based on the weight of the composition.

In some embodiments, one or more actives, alone or in combination, may be present in the composition according to the disclosure from about 0.05% to about 50% by weight, alternatively from about 0.05% to about 2.5% by weight, alternatively from about 0.1% to about 2%, alternatively from about 0.25% to about 1.5%, alternatively from about 0.5% to about 1.25%, or any suitable combination, sub-combination, range, or sub-range thereof by weight, based on the weight of the composition.

In some embodiments, one or more other components, such as preservatives, vitamins, and the like, alone or in combination, may be present in the composition according to the disclosure from about 0.05% to about 50% by weight, alternatively from about 0.05% to about 25% by weight, alternatively from about 0.1% to about 10%, alternatively from about 0.25% to about 5%, alternatively from about 0.5% to about 3.5%, or any suitable combination, sub-combination, range, or sub-range thereof by weight, based on the weight of the composition. In some exemplary embodiments, preservatives may include sodium salicylate, and vitamins may include ascorbic acid, tocopherol and combinations thereof.

Method of Application

In accordance with the disclosure, the composition is applied to keratinous substrate and rubbed with fingers to try to spread the composition as a thin coating. Before being rubbed, the composition starts thick. The composition provides a transformative texture that thins out and becomes smooth upon rubbing. The texture leaves a satin/velvet residue and a silky feeling. Due to the transformative texture, the composition is easily spreadable to keratinous substrate.

Articles of Manufacture

In accordance with the various embodiments, the composition may be provided in a kit or other article of manufacture, such as, a mask, cream, or lotion.

In accordance with the various embodiments, a cosmetic composition is in a form including a suspension, lotion, cream, serum, essence, gel, stick, spray, ointment, paste, foam, mousse, cream, wipe, patch, strip, film-forming product, facial masks or skin masks.

The following examples are intended to further illustrate the present invention. They are not intended to limit the invention in any way. Unless otherwise indicated, all parts are by weight.

EXAMPLES

Representative examples of inventive and comparative compositions are shown in Tables 1-3.

TABLE 1

Inventive and Comparative examples

|  | Inventive Example 1 | Comparative Example 1 | Comparative Example 2 | Comparative Example 3 | Comparative Example 4 |
| --- | --- | --- | --- | --- | --- |
| *Butyrospermum parkii* (shea) butter | 2% | 0% | 5% | 0% | 15% |
| *Theobroma cacao* (cocoa) seed butter | 1% | 0% | 5% | 0% | 15% |
| *Sesamum indicum* (sesame) seed oil | 3% | 5% | 0% | 15% | 0% |
| Caprylic/capric triglyceride (oil) | 4% | 5% | 0% | 15% | 0% |
| Non-ionic surfactant | 6.73% | 6.73% | 6.73% | 6.73% | 6.73% |
| Thickener | 0.70% | 0.70% | 0.70% | 0.70% | 0.70% |
| Active compound | 1.10% | 1.10% | 1.10% | 1.10% | 1.10% |
| Preservative | 1% | 1% | 1% | 1% | 1% |
| Silicon | 0.15% | 0.15% | 0.15% | 0.15% | 0.15% |
| Vegetable extract | 0.01% | 0.01% | 0.01% | 0.01% | 0.01% |
| Vitamin | 0.60% | 0.60% | 0.60% | 0.60% | 0.60% |
| Organic solvent | 12.30% | 12.30% | 12.30% | 12.30% | 12.30% |
| Water | q.s. | q.s. | q.s. | q.s. | q.s. |
| Finishing feel | Velvet/satin | Oily | Hard to rub in | Very oily | Very oil |
| Transformative? | Yes | No | No | No | No |

TABLE 2

Inventive and Comparative examples (cont'd)

|  | Comparative Example 5 | Comparative Example 6 | Inventive Example 2 | Inventive Example 3 | Inventive Example 4 |
| --- | --- | --- | --- | --- | --- |
| *Butyrospermum parkii* (shea) butter | 5% | 5% | 5% | 5% | 4% |
| *Theobroma cacao* (cocoa) seed butter | 5% | 5% | 5% | 5% | 0% |

TABLE 2-continued

Inventive and Comparative examples (cont'd)

| | Comparative Example 5 | Comparative Example 6 | Inventive Example 2 | Inventive Example 3 | Inventive Example 4 |
|---|---|---|---|---|---|
| *Sesamum indicum* (sesame) seed oil | 5% | 3.75% | 7.5% | 10% | 1% |
| Caprylic/capric triglyceride (oil) | 5% | 3.75% | 7.5% | 10% | 6% |
| Non-ionic surfactant | 6.73% | 6.73% | 6.73% | 6.73% | 6.73% |
| Thickener | 0.70% | 0.70% | 0.70% | 0.70% | 0.70% |
| Active compound | 1.10% | 1.10% | 1.10% | 1.10% | 1.10% |
| Preservative | 1% | 1% | 1% | 1% | 1% |
| Silicon | 0.15% | 0.15% | 0.15% | 0.15% | 0.15% |
| Vegetable extract | 0.01% | 0.01% | 0.01% | 0.01% | 0.01% |
| Vitamin | 0.60% | 0.60% | 0.60% | 0.60% | 0.60% |
| Organic solvent | 12.30% | 12.30% | 12.30% | 12.30% | 12.30% |
| Water | q.s. | q.s. | q.s. | q.s. | q.s. |
| Finishing feel | Oily | Oily | Velvet/satin | Velvet/satin | Velvet/satin |
| Transformative? | No | No | Yes | Yes | Yes |

TABLE 3

Inventive examples (cont'd)

| | Inventive Example 5 | Inventive Example 6 |
|---|---|---|
| *Butyrospermum parkii* (shea) butter | 2.5% | 2% |
| *Theobroma cacao* (cocoa) seed butter | 1% | 1% |
| *Sesamum indicum* (sesame) seed oil | 1.5% | 1% |
| Caprylic/capric triglyceride (oil) | 5% | 5% |
| Non-ionic surfactant | 6.73% | 6.73% |
| Thickener | 0.70% | 0.70% |
| Active compound | 1.10% | 1.10% |
| Preservative | 1% | 1% |
| Silicon | 0.15% | 0.15% |
| Vegetable extract | 0.01% | 0.01% |
| Vitamin | 0.60% | 0.60% |
| Organic solvent | 12.30% | 12.30% |
| Water | q.s. | q.s. |
| Finishing feel | Velvet/satin | Velvet/satin |
| Transformative? | Yes | Yes |

Inventive Examples 1-6 with both butters and oils were tested. Similarly, Comparative Examples 1-6 with either butters or oils were tested. For all examples, complex modulus versus oscillation strain were plotted to investigate the transformative texture. A change of complex modulus over a large range of strain gives rise to a transformative texture. Inventive Examples 1-6 showed the transformative texture but Comparative Examples 1-6 did not.

Consumer evaluation testing revealed that Inventive Example 1 left a unique silky residue to provide velvet/satin finishing feel. Inventive Example 1 was also reported to create an occlusive barrier to trap in moisture. Consumers further claimed that Inventive Example 1 provides an ideal canvas for their foundation.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition comprising:
    an aqueous phase comprising water present from about 40 to about 80% and at least one water soluble ingredient including at least one non-ionic surfactant;
    an oil phase comprising:
        a transformative agent comprising at least 2% of at least one butter and at least 4%, combined, of at least one oil and at least one triglyceride, the transformative agent having a butter to oil and triglyceride ratio of from about 2:5 to 7:10 and triglyceride to oil ratio of from 1:1 to 6:1;
    at least one thickener employed in an amount from about 0.5 to about 5%; and
    at least one organic solvent, all amounts by weight, based on the weight of the composition,
    wherein the cosmetic composition has a transformative texture,
    wherein the at least one triglyceride includes at least one of dicaprylyl capric triglyceride or caprylic/capric triglyceride, and
    wherein the at least one oil is selected from the group consisting of *Helianthus annuus* (sunflower) seed oil, *Sesamum indicum* (sesame) seed oil, coconut oil, jojoba oil, isopropyl palmitate, isononyl isononanoate, apricot oil, dicaprylyl carbonate, and combinations thereof.

2. The composition of claim 1, wherein the at least one non-ionic surfactant is selected from the group consisting of stearic acid, polysorbate 20, glyceryl stearate, PEG-100 stearate, sorbitan stearate, cetearyl alcohol, ceteareth-20 and combinations thereof.

3. The composition of claim 1, wherein the at least one butter is selected from the group consisting of butyrospermum parkii (shea) butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, macadamia nut butter, mango butter and combinations thereof.

4. The composition of claim 1, wherein the at least one oil includes *Sesamum indicum* (sesame) seed oil.

5. The composition of claim 1, wherein the at least one thickener is selected from the group consisting of xanthan gum, carbomer and combinations thereof.

6. The composition of claim 1, wherein the at least one organic solvent is selected from the group consisting of butylene glycol, C12-15 alkyl benzoate, glycerin, propylene glycol, caprylyl glycol and combinations thereof.

7. The composition of claim 1, wherein the at least one non-ionic surfactant is employed in an amount of from about 1 to 20 wt %.

8. The composition of claim 1, wherein the at least one butter is employed in an amount of from about 3 to about 10 wt %, and the at least one oil and the at least one triglyceride, combined, are employed in an amount of from about 3 to about 10 wt %.

9. The composition of claim 1, wherein the at least one thickener is employed in an amount of from about 0.5 to about 4.5 wt %.

10. The composition of claim 1, wherein the at least one organic solvent is employed in an amount of from about 10 to about 30 wt %.

11. The composition of claim 1, wherein the at least one triglyceride comprises caprylic/capric triglyceride.

12. The composition of claim 1, further comprising one or more additional components selected from the group consisting of actives selected from humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof.

13. The composition of claim 12 further comprising one or more actives selected from the group consisting of sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

14. A cosmetic composition comprising:
an aqueous phase comprising water present from about 40 to 80% and at least one water soluble ingredient including from about 1 to 20% of at least one non-ionic surfactant;
an oil phase comprising:
a transformative agent comprising from 2 to about 9% of at least one butter and from 4 to about 10%, combined, of at least one oil and at least one triglyceride, the transformative agent having a butter to oil and triglyceride ratio of from about 2:5 to 7:10 and triglyceride to oil ratio of from 1:1 to 6:1;

from about 0.5 to about 5% of at least one thickener; and
from about 10 to about 30% of at least one organic solvent, all amounts by weight, based on the weight of the composition,
wherein the cosmetic composition has a transformative texture,
wherein the at least one triglyceride includes at least one of dicaprylyl capric triglyceride or caprylic/capric triglyceride, and
wherein the at least one oil is selected from the group consisting of *Helianthus annuus* (sunflower) seed oil, *Sesamum indicum* (sesame) seed oil, coconut oil, jojoba oil, isopropyl palmitate, isononyl isononanoate, apricot oil, dicaprylyl carbonate, and combinations thereof.

15. The composition of claim 14, wherein the at least one triglyceride comprises caprylic/capric triglyceride.

16. The composition of claim 14, further comprising one or more additional components selected from the group consisting of actives selected from humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof.

17. The composition of claim 16, further comprising one or more actives selected from the group consisting of sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

18. A method of preparing a cosmetic composition comprising:
providing an aqueous phase comprising water present from about 40 to 80% by weight, based on the weight of the composition, and at least one water soluble ingredient including at least one non-ionic surfactant;
providing an oil phase comprising: at least 2% of at least one butter and at least 4%, combined, of at least one oil and at least one triglyceride, each by weight, based on the weight of the composition, and having a butter to oil and triglyceride ratio of from about 2:5 to 7:10 and triglyceride to oil ratio of from 1:1 to 6:1;
providing at least one thickener present from about 0.5 to about 5% by weight, based on the weight of the composition, and at least one organic solvent; and
mixing the provided aqueous phase, oil phase, thickener, and organic solvent to form the cosmetic composition,
wherein the cosmetic composition has a transformative texture,
wherein the at least one triglyceride includes at least one of dicaprylyl capric triglyceride or caprylic/capric triglyceride, and
wherein the at least one oil is selected from the group consisting of *Helianthus annuus* (sunflower) seed oil, *Sesamum indicum* (sesame) seed oil, coconut oil, jojoba oil, isopropyl palmitate, isononyl isononanoate, apricot oil, dicaprylyl carbonate, and combinations thereof.

19. The method of claim 18, wherein the triglyceride comprises caprylic/capric triglyceride.

20. A method for treating or hydrating skin, improving or maintaining the hydration of skin, improving or maintaining the texture of the skin, or improving or maintaining the skin barrier function, the method comprising applying the composition of claim 1 onto skin.

21. A cosmetic composition comprising:
oil and aqueous phases that provide a transformative texture, including:
a transformative agent comprising from 2 to about 10% of at least one butter and from 4 to about 10%, combined, of at least one oil and at least one triglyceride, the transformative agent having a butter to oil ratio of from about 2:5 to 7:10 and triglyceride to oil ratio of from 1:1 to 6:1;
water present from about 40 to 80%;
at least one non-ionic surfactant present from about 1 to 20%;
at least one thickener present from about 0.5 to about 5%; and
at least one organic solvent present from about 10 to about 30%, all amounts by weight, based on the weight of the composition,
wherein the cosmetic composition has a transformative texture,
wherein the at least one triglyceride includes at least one of dicaprylyl capric triglyceride or caprylic/capric triglyceride, and
wherein the at least one oil is selected from the group consisting of *Helianthus annuus* (sunflower) seed oil, *Sesamum indicum* (sesame) seed oil, coconut oil, jojoba oil, isopropyl palmitate, isononyl isononanoate, apricot oil, dicaprylyl carbonate, and combinations thereof.

22. The cosmetic composition of claim 21, wherein the composition comprises a combination of butters selected from the group consisting of butyrospermum parkii (shea) butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, macadamia nut butter, mango butter, and combinations thereof, each butter in the combination present from about 1 to about 10 wt %.

23. The cosmetic composition of claim 21, wherein the at least one oil comprises *Sesamum indicum* (sesame) seed oil.

24. The cosmetic composition of claim 21, wherein the composition comprises a combination of non-ionic surfactants selected from the group consisting of stearic acid, polysorbate 20, glyceryl stearate, PEG-100 stearate, sorbitan stearate, cetearyl alcohol, ceteareth-20, the combination present from about 1 to about 20 wt %.

25. The cosmetic composition of claim 21, wherein the composition comprises a combination of organic solvents selected from the group consisting of butylene glycol, C12-15 alkyl benzoate, glycerin, propylene glycol, caprylyl glycol, and combinations thereof, the combination present from about 10 to about 30 wt %.

26. The cosmetic composition of claim 21, wherein the composition comprises one or a combination of thickeners selected from the group consisting of xanthan gum, and carbomer.

27. The cosmetic composition of claim 21, wherein the composition comprises:
a combination of butters selected from the group consisting of butyrospermum parkii (shea) butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, macadamia nut butter, and mango butter, and combinations thereof, each butter in the combination present from about 1 to about 10 wt %;
a combination of oils and triglycerides including *Sesamum indicum* (sesame) seed oil, and caprylic/capric triglyceride;
a combination of non-ionic surfactants selected from the group consisting of stearic acid, polysorbate 20, glyceryl stearate, PEG-100 stearate, sorbitan stearate, cetearyl alcohol, ceteareth-20, the combination present from about 4 to about 11 wt %;
a combination of organic solvents selected from the group consisting of butylene glycol, C12-15 alkyl benzoate, glycerin, propylene glycol, caprylyl glycol, and combinations thereof, the combination present from about 10 to about 30 wt %; and
one or a combination of thickeners selected from the group consisting of xanthan gum, and carbomer.

* * * * *